US006913920B2

(12) United States Patent
Shamoun et al.

(10) Patent No.: US 6,913,920 B2
(45) Date of Patent: Jul. 5, 2005

(54) **CULTURE, FORMULATION, AND DELIVERY TECHNIQUES OF *VALDENSINIA HETERODOXA*, AND ITS USE AS A BIOLOGICAL CONTROL AGENT OF SALAL (*GAULTHERIA SHALLON*)**

(75) Inventors: Simon Francis Shamoun, Victoria (CA); Susanne Vogelgsang, Gampelen (CH)

(73) Assignee: Her Majesty the Queen in right of Canada, as represented by the Minister of Natural Resources Canada, Canadian Forest Service, Ontario (CA)

( * ) Notice: Subject to any disclaimer, the term of this patent is extended or adjusted under 35 U.S.C. 154(b) by 270 days.

(21) Appl. No.: 10/155,992

(22) Filed: May 29, 2002

(65) Prior Publication Data

US 2002/0192804 A1 Dec. 19, 2002

Related U.S. Application Data

(60) Provisional application No. 60/293,512, filed on May 29, 2001.

(51) Int. Cl.[7] .................................................. C12N 1/14
(52) U.S. Cl. ..................... 435/254.1; 424/93.5; 504/117
(58) Field of Search ...................... 435/254.1; 424/93.5; 504/117

(56) References Cited

U.S. PATENT DOCUMENTS 5,993,802 A * 11/1999 Mallett ....................... 424/93.5

OTHER PUBLICATIONS

Norvell, L. L. and S. A. Redhead (1994). *Valdensinia heterodoxa* (*Sclerotiniaceae*) in the United Norvell et al., Canadian Journal of Forest Research 24(9): 1981–1983.*
Redhead, S. A. 1979. Mycological observations: 1, on *Cristulariella*; 2, on *Valensinia*; 3, on *Neolecta. Mycologia* 71:1248–1253.*
Shamoun, S. F. Canadian Journal of Plant Pathology, (Jun. 2000) vol. 22, No. 2, pp. 192.*

* cited by examiner

*Primary Examiner*—Irene Marx

(57) ABSTRACT

The invention disclosed relates to a naturally occurring fungus, *Valdensinia heterodoxa*, and to its culture, formulation and delivery systems, as well as its use as a biocontrol agent for salal (*Gaultheria shallon* Pursh.).

13 Claims, 1 Drawing Sheet

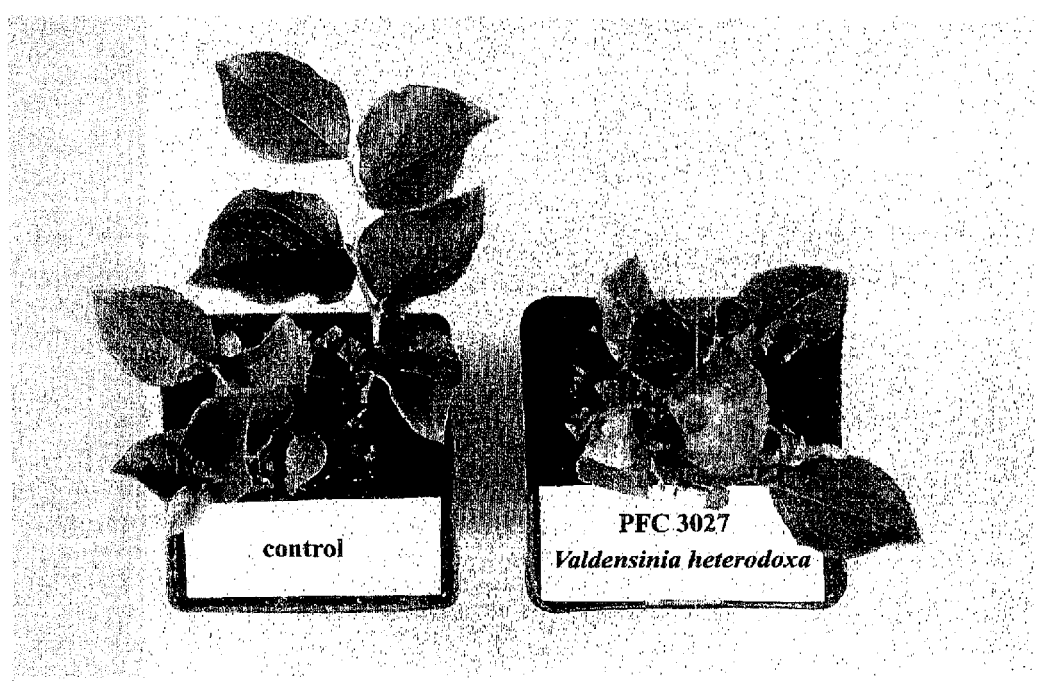

CULTURE, FORMULATION, AND DELIVERY TECHNIQUES OF VALDENSINIA HETERODOXA, AND ITS USE AS A BIOLOGICAL CONTROL AGENT OF SALAL (GAULTHERIA SHALLON)

This application claims the benefit of U.S. provisional No. 60/293,512, filed May 29, 2001.

BACKGROUND OF THE INVENTION

The present invention relates to the naturally occurring fungus, Valdensinia heterodoxa, and in particular to its use as a biocontrol agent for salal (Gaultheria shallon Pursh.).

Forest management has become increasingly intensive in order to maximize forest productivity and sustainability. The past few decades have seen significant changes in forest management practices, especially in the area of site preparation, the use of chemical herbicides, and development of new forest harvesting systems. Competition from non-commercial or competing forest vegetation is a major problem at conifer regeneration sites following harvest in plantations. This competition results in conifer mortality, reduced growth, delays in harvesting time, increased costs related to forest management, and decreases in annual allowable cut (Wall et al. 1992). Management of competing forest vegetation can take various forms, including removal by mechanical or manual brushing and chemical herbicides. These methods have distinct disadvantages such as non-target effects and public concerns about the negative impacts of using herbicides in pristine forest ecosystems. Hence, there is a growing need for alternative management strategies for competing vegetation that are cost-effective, environmentally safe, economically feasible, and sustainable (Watson and Wall 1995). One viable option is the use of naturally occurring plant pathogens as biological control agents which, if successful, are expected to result in increased early conifer growth rate and a shorter rotation age of commercially valuable crop trees (Shamoun 2000).

Salal (Gaultheria shallon Pursh.), a perennial, ericaceous shrub, is a serious competitor with conifer seedlings in coastal British Columbia. Generally, it competes with trees for water and nutrients and removal of salal leads to enhanced conifer growth (McDonald 1990). Salal is difficult to control with current mechanical methods due to its extensive root system leading to quick reestablishment through layering, sprouting, and suckering (D'Anjou 1990). Chemical herbicides are often ineffective since salal's thick and leathery leaves reduce herbicide translocation (D'Anjou 1990). Hence, salal can be considered a suitable target weed for biological control using fungal pathogens.

Numerous fungal species have been isolated from salal plants, including Mycosphaerella gaultheriae (Haeussler et al. 1990), Phyllosticta pyrolae Ellis et Everh. (Petrini et al. 1982), Phytophthora cinnamoni Rands (Lindermann & Zeitoun 1977), and Valdensinia heterodoxa Peyr. (Readhead 1974).

In 1999, a survey was conducted to collect and identify the mycobiota associated with salal from various locations on Vancouver Island (Shamoun et al. 2000).

Fungal pathogens isolated from diseased leaf and stem tissue were subsequently assessed for their virulence on salal. From the tested fungi, Valdensia heterodoxa (PFC 3027) caused substantial leaf damage on both detached leaves and intact salal plants (Vogelgsang et al. 2001).

SUMMARY OF THE INVENTION

According to an embodiment of the present invention, a biologically pure isolate of the naturally occurring fungus, Valdensinia heterodoxa, having all of the identifying characteristics of IDAC Deposit Accession no. IDA 180402, is provided.

According to a further embodiment of the invention, a herbicidal composition containing as active ingredient, Valdensinia heterodoxa, having all of the identifying characteristics of IDAC Deposit Accession no. IDA 180402, is provided.

According to yet another embodiment of the present invention, a herbicidal composition for controlling salal (Gaultheria shallon Pursh) is also provided, the composition comprising as active ingredient, an effective amount of a culture of V. heterodoxa on an agriculturally and environmentally acceptable solid growth substrate capable of supporting growth of the fungus, containing a cereal grain, e.g., oatmeal.

According to yet another embodiment of the present invention, a method for controlling salal (Gaultheria shallon Pursh.), is also provided, the method comprising applying to a salal plant or to a salal plant locus, an effective amount of a herbicidal composition containing as active ingredient, a biologically pure isolate of the fungus Valdensinia heterodoxa having all of the identifying characteristics of IDAC Deposit Accession no. IDA 180402.

According to another embodiment of the present invention, a method is provided for isolating Valdensinia heterodoxa from nature in biologically pure form.

According to yet another aspect of the invention, salal plant tisue e.g. leaves and stems colonized by V. heterodoxa is used as an inoculum delivery mechanism to control salal.

According to yet another embodiment of the present invention, an inoculation of salal plant tissue, e.g., leaf pieces, with mycelium of V. heterodoxa produced from cereal grain, e.g., oatmeal, containing growth media e.g. agar.

We have also found that using additional solid substrates infected with the fungus such as: 1) alder saw dust; 2) fir saw-dust; 3) vermiculite powder; 4) rice grain; 5) rolled oats; and 6) whole oats. Again, the results showed that the most effective solid substrate for formulation and conidia production and discharge was on salal leaves and stems. There was also production and discharge of conidia on alder saw dust and fir-saw dust, but was not significant compared to salal leaves and stems.

Further, we have found that a medium containing rolled oats as the only carbohydrate source (e.g., water agar containing a few rolled oats on the surface) has triggered the sporulation of Valdensinia heterodoxa.

According to yet another aspect of our invention, we have found to advantage that innoculation of plant materials, such as leaves and stems as a delivery mechanism. Typically, in the prior art, non-host materials are used such as cereal grains, alginate pellets and vermiculite.

As already mentioned above, in the culturing method itself, the use of oatmeal in the medium, lower incubation temperature and the use of host-tissue for final formulation and delivery technologies are novel for this pathosystem (*Valdensinia heterodoxa*-Salal).

It is also significant that there is a cut-off temperature above which sporulation is inhibited. Also, in the case of *Valdensinia heterodoxa*, for conidia discharge, the optimum for conidia discharge at rather low temperature is unusual for the majority of fungal pathogens. More importantly, as will be apparent from the examples which follow, sporulation and discharge are severely inhibited above and below the determined optima.

It is also interesting that alternating light and dark treatments resulted in significantly lower growth rates, sporulation, and conidia discharge. See Table 2.

DEPOSIT INFORMATION

The above referenced Deposit was made with the International Depository Authority of Canada(IDAC), 1015 Arlington street, Winnipeg, Manitoba, R3E 3R2, Canada, under the auspices of the Budapest Treaty, under accession no. 18042. The Deposit was received by the IDAC on 18 Apr. 2002, and was tested and confirmed to be viable on 22 Apr. 2002. The deoosited material is of aenus/soecies *Valdensinia heterodoxa*, sub-division Ascomycete. order Sclerotiniaceae.

BRIEF DESCRIPTION OF THE DRAWING

The FIGURE illustrates the effect of *Valdensinia heterodoxa* from colonized salal leaf pieces on intact salal plants 14 days post-inoculation (dpi). For each treatment, 3 g of uninoculated (control or colonized (PFC isolate 3027) leaf pieces were placed beneath salal leaves. First disease symptoms were observed at 4 dpi.

DETAILED DESCRIPTION OF THE INVENTION

Isolation of *Valdensinia heterodoxa* from Diseased Leaf Samples

*Valdensinia heterodoxa* (PFC 3027) having all of the identifying characteristics of IDAC Deposit accession no. IDA 180402 was isolated from salal leaf tissues in biologically pure form, by surface sterilizing small pieces of infected tissue, plating them onto potato dextrose agar (PDA) or malt extract agar (MEA) and incubating in the dark at 20° C. Emerging colonies were subcultured onto PDA plates, and then transferred to PDA slants for long-term storage at 5° C.

Starter Cultures of *Valdensinia heterodoxa*

Cultures of *V. heterodoxa* (PFC 3027) were initiated by placing small (*V. heterodoxa*) mycelium pieces from potato dextrose agar (PDA) slants maintained at 4° C. on salal PDA (SPDA; PDA amended with 40 g fresh, blended salal leaf and stem material/L dH$_2$O). Fungal cultures were grown at 19/13° C. (day/night) with a 12 h day photoperiod (180–200 $\mu$Em$^{-2}$s$^{-1}$). Eight days after inoculation, mycelial plugs of 5-mm diameter were transferred onto weak oatmeal agar (WOA; 15 g oatmeal agar and 12 g agar/L dH$_2$O) and incubated at the desired conditions, depending on the experiment.

Effect of Temperature on Growth, Sporulation, and Conidia Discharge of *Valdensinia heterodoxa*

Materials and Methods

Growth chambers were programmed at 11/6, 14/9, 17/12, and 20/15° C., respectively, with a 12 h day$^{-1}$ photoperiod (180–200 $\mu$Em$^{-2}$ s$^{-1}$). Fungal cultures of *V. heterodoxa* were initiated on SPDA and transferred onto WOA as described above. At 3, 6, and 9 days post-inoculation (dpi), mycelial radial growth (colony diameter), total number of conidia, and number of discharged conidia adhering to the lid of the Petri dish were determined. For each temperature treatment, five replicates were used and the experiment was performed twice. Data were subjected to a one-way analysis of variance (ANOVA). In case of failed normality or equal variance tests, a Kruskal-Wallis one-way ANOVA on ranks was used instead. Differences between treatment means were evaluated by a Student-Newman-Keuls multiple comparison procedure (P=0.05).

Results

Throughout the experiment, mycelial radial growth was greatest at the higher temperature regimes of 17/12 and 20/15° C. and was strongly inhibited at 11/6° C. Similarly, total sporulation was improved at higher temperatures. However, conidia discharge displayed a clear optimum at 17/12° C. and declined substantially at both temperatures above and below this regime. Differences in sporulation were observed as early as 3 dpi but more pronounced towards later evaluation dates. The results of both trials are summarized in Table 1.

TABLE 1

Effect of day/night temperature on mycelial growth, sporulation, and conidia discharge of *Valdensinia heterodoxa* (PFC 3027) at different days post-inoculation (dpi).

|  | Temperature (° C.)[1] | Trial 1 | | | Trail 2 | | |
| --- | --- | --- | --- | --- | --- | --- | --- |
|  |  | 3 dpi[2] | 6 dpi | 9 dpi | 3 dpi | 6 dpi | 9 dpi |
| Colony diameter (cm) | 11/6 | 1.2 a | 1.6 a | 2.1 a | 1.1 a | 1.9 a | 2.5 a[3] |
|  | 14/9 | 1.7 b | 2.9 b | 4.4 b | 1.5 b | 2.9 b | 4.1 b |
|  | 17/12 | 2.0 b | 3.5 b | 4.6 b | 1.9 c | 3.6 c | 4.7 c |
|  | 20/15 | 2.0 b | 3.5 b | 4.7 b | 1.6 b | 2.1 a | 2.4 a |
| Total number of conidia | 11/6 | 2.4 a | 15.0 a | 18.0 a | 11.6 b | 29.4 a | 44.0 a |
|  | 14/9 | 10.8 ab | 23.2 a | 108.6 a | 12.4 b | 48.8 a | 174.0 a |
|  | 17/12 | 23.6 b | 121.2 b | 318.0 b | 3.0 a | 206.4 b | 862.4 b |

TABLE 1-continued

Effect of day/night temperature on mycelial growth, sporulation, and conidia discharge of *Valdensinia heterodoxa* (PFC 3027) at different days post-inoculation (dpi).

| | Temperature (° C.)[1] | Trial 1 | | | Trail 2 | | |
|---|---|---|---|---|---|---|---|
| | | 3 dpi[2] | 6 dpi | 9 dpi | 3 dpi | 6 dpi | 9 dpi |
| | 20/15 | 26.6 b | 158.6 b | 381.6 b | 0.0 a | 4.2 a | 13.2 a |
| Number of | 11/6 | 0.0 a | 0.8 a | 0.8 a | 0.2 a[3] | 1.6 ab[3] | 2.4 b[3] |
| discharged | 14/9 | 0.4 a | 3.2 a | 3.8 ab | 0.6 a | 3.4 ab | 9.0 b |
| conidia | 17/12 | 4.2 a | 4.8 a | 11.6 b | 0.0 a | 6.8 b | 72.0 c |
| | 20/15 | 2.8 a | 3.4 a | 5.2 ab | 0.0 a | 0.0 a | 0.2 a |

[1]Temperature A/B describes day/night temperatures with a 12 h photoperiod.
[2]Means in one column and for one parameter followed by the same letter are not significantly different according to a one-way ANOVA procedure followed by a Student-Newman-Keuls multiple comparison procedure.
[3]As in footnote 2 but according to a Kruskal-Wallis one-way ANOVA on ranks procedure.

Effect of Photoperiod on Growth, Sporulation, and Conidia Discharge of *Valdensinia heterodoxa*

Materials and Methods

Three photoperiod conditions including continuous light, alternating light/dark (12 h day$^{-1}$ photoperiod), and continuous darkness were investigated. Cultures of *V. hetero-doxa* were initiated on SPDA and transferred onto WOA as described above. Fungal cultures were grown in a single chamber programmed at 17/12° C. with 24 h day$^{-1}$ light (180 $\mu$Em$^{-2}$s$^{-1}$). The treatment of continuous darkness was achieved by wrapping the Petri dishes in aluminium foil. Petri dishes assigned to alternating light conditions were unwrapped daily at the start of the higher temperature cycle. Evaluation of mycelial growth, sporulation, and conidia discharge was performed as described above. For each photoperiod treatment, five replicates were used and the experiment was performed twice. Data were analyzed as for the previous experiment.

Results

Radial mycelial growth was moderately slower and total sporulation and conidia discharge were strongly inhibited by continuous darkness. Although all evaluated parameters were improved by a continuous light treatment, differences between and continuous and alternating light were not always significant (Table 2). As in the temperature experiment, differences were observed as early as 3 dpi. Sporulation data at later dates were highly variable for any of the light treatments. Results of both trials are summarized in Table 2.

TABLE 2

Effect of photoperiod duration on mycelial growth, sporulation, and conidia discharge of *Valdensinia heterodoxa* (PFC 3027) at different days post-inoculation (dpi).

| | Light treatment[1] | Trial 1 | | | Trial 2[3] | | |
|---|---|---|---|---|---|---|---|
| | | 3 dpi[2] | 6 dpi | 9 dpi | 3 dpi | 6 dpi | 9 dpi |
| Colony diameter (cm) | Light | 2.3 a | 4.2 a | 5.2 a | 1.7 a | 3.5 a | 4.5 a |
| | Alternating | 2.0 b | 3.6 b | 4.9 b | 1.6 a | 3.1 ab | 4.1 a |
| | Dark | 2.0 b | 3.4 b | 4.7 b | 1.6 a | 2.8 b | 3.7 b |
| Total number of conidia | Light | 64.8 a | 428.2 a | 865.0 a | 48.4 a | 227.6 a | 519.0 a |
| | Alternating | 8.8 b | 137.8 b | 645.2 a | 6.2 b | 49.4 b | 168.0 b |
| | Dark | 0.2 b | 2.4 b | 51.6 b | 0.4 c | 5.2 c | 45.8 c |
| Number of discharged conidia | Light | 5.4 a[3] | 35.0 a | 126.4 a | 3.0 a | 13.2 a | 17.2 a |
| | Alternating | 0.6 b | 5.2 b | 51.0 ab | 0.6 b | 3.6 b | 5.2 b |
| | Dark | 0.0 b | 0.0 b | 1.6 b | 0.0 b | 0.2 c | 4.8 b |

[1]Light, alternating, dark: continuous light, 12 h photoperiod, and continuous dark, respectively. Temperatures for all treatments were 17/12° C. day/night.
[2]Means in one column and for one parameter followed by the same letter are not significantly different according to a one-way ANOVA procedure followed by a Student-Newman-Keuls multiple comparison procedure.
[3]As in footnote 2 but according to a Kruskal-Wallis one-way ANOVA on ranks procedure.

Solid-Based Formulation and Delivery Technique of *Valdensinia heterodoxa*

Materials and Methods

Starter cultures of *V. heterodoxa* on SPDA were initiated as described above. Erlenmeyer flasks containing 250 mL of liquid weak oatmeal medium (WOM; 20 g blended rolled oats/L dH$_2$O) were inoculated with 10 mycelial plugs from the starter cultures. Flasks were placed on a shaker (125 rpm) at 19/13° C. with a 12 h day$^{-1}$ photoperiod (180–200 $\mu$Em$^{-2}$ s$^{-1}$).

After 7 days, resulting mycelium was harvested on double-layered cheesecloth and blended in a Waring blender for 20 sec at high speed. Five mL of wet mycelium was added to Erlenmeyer flasks containing autoclaved salal leaf pieces (7 g litter+5 mL $dH_2O$). The fungal inoculum was incubated as described above and flasks were shaken daily. After 14 days, the colonized leaf material was air-dried for 2 days in a fume hood.

Salal seedlings were grown outside in 8 cm pots containing peat-vermiculite-sand (1:1:1) and a low rate of slow release fertilizer. Plants of similar size were selected and transferred into a growth chamber at the original conditions.

Fungal inoculum was applied below salal leaves. For potted salal plants, usually several leaves protrude farther than the pot rim, hence, a structure was built beyond the rim to ensure that all leaves could be reached by discharging conidia. Plastic sheets (coroplast) were cut into 14×14 cm pieces with a 6×6 cm hole in the centre. To provide a rougher surface for the leaf pieces to be placed onto, cheesecloth was cut into the same outside dimensions as the coroplast with a ¾ slit in the centre. Both coroplast and cheesecloth were carefully placed around the plant and fixed with a pin. For each plant, 3 g of dried leaf pieces were applied onto the cheesecloth and watered with $dH_2O$ from a spraying bottle. Uninoculated leaf pieces served as the control treatment. For each treatment, five replicate plants were used. Pots were then transferred to a dew chamber (100% relative humidity, 20±1° C.) for 24 h; and subsequently covered with clear plastic bags and the ends tucked under the base of the pots. After the dew treatment, pots were moved back to the original growth chamber. Plastic bags were removed daily for a few minutes to ensure proper aeration. Leaf damage was evaluated 14 dpi, based on the percentage of necrotic leaf area. Data were analyzed using a Kruskal-Wallis one-way analysis of variance on ranks followed by a Student-Newman-Keuls multiple comparison procedure in order to evaluate differences between treatment means (P=0.05).

Results

First disease symptoms on salal plants developed 4 dpi and necroses expanded quickly over the next days, whereas no symptoms were observed on the control plants (FIGURE). Older leaves with thicker cuticle became infected as well, but necroses did not expand as fast compared with young leaves. The origin of the necrosis was easily identified by the discharged conidium still attached to the leaf surface in the centre of the necrosis. Some leaves with their upper surface facing down, developed disease symptoms as well. As the stomata of salal are only found on the lower leaf surface, it is assumed that conidia of *V. heterodoxa* are able to penetrate their host directly. In trial 1 and trial 2, plants exposed to the fungal inoculum developed on average 33 and 39% leaf damage, respectively.

The observed leaf damage in this study is rather low compared with a spray application of other potential bioherbicides in which plants are usually completely covered with fungal propagules. Although most necroses developed rapidly, many leaves were not infected until the end of the experiment. On those leaves, very few conidia were found, due to either insufficient sporulation and/or loss of discharged conidia.

The findings of this research confirm the potential of *V. heterodoxa* to be used as a biological control agent for salal, and in particular, the use of colonized leaf pieces as an inoculum source and delivery technique.

REFERENCES

D'Anjou, B 1990. Control of salal. In: Vegetation Management: An Integrated Approach—Proceedings of the Fourth Annual Vegetation Management Workshop (E. Hamilton, ed.). Forest Research Development Agreement Report 109: 25–26. Forestry Canada and British Columbia Ministry of Forests, Victoria, BC, Canada.

Haeussler, S, Coates, D, and Mather, J 1990. Autecology of common plants in British Columbia: a literature review. Forest Research Development Agreement Report 158: 96–102.

Lindermann, R G and Zeitoun, F 1977. *Phytophthora cinnamoni* causing root rot and wilt of nursery-grown native western azalea and salal. Plant Disease Reports 61: 1045–1048.

McDonald, M A 1990. Competition for nutrients and chemical interference by salal (*Gaultheria shallon* Pursh.). In: Vegetation Management: An Integrated Approach—Proceedings of the Fourth Annual Vegetation Management Workshop (E. Hamilton, ed.). Forest Research Development Agreement Report 109: 16–17. Forestry Canada and British Columbia Ministry of Forests, Victoria, BC, Canada.

Petrini, O, Stone, J, and Carroll, F E 1982. Endophytic fungi in evergreen shrubs in western Oregon: a preliminary study. Canadian Journal of Botany 60: 789–796.

Readhead, S 1974. Epistolae mycologicae IV. *Valdensinia heterodoxa* Peyr. (Sclerotiniaceae). Syesis 7: 235–238.

Shamoun, S F 2000. Application of biological control to vegetation management in forestry. In: Proceedings of the Tenth International Symposium on Biological Control of Weeds, 4–14 Jul. 1999, Montana State University, Bozeman, Mont., USA, pp. 87–96.

Shamoun, S F, Countess, R E, Vogelgsang, S, and Oleskevich, C 2000. The mycobiota of salal (*Gaultheria shallon*) collected on Vancouver Island and the exploitation of fungal pathogens for biological control. The Canadian Phytopathological Society, Annual Meeting, Victoria, BC, Canada, Canadian Journal of Plant Pathology 22: 192 (abstract).

Wall, R E, Prasad, R, and Shamoun, S F 1992. The development and potential role of mycoherbicides for forestry. Forestry Chronicle 68: 736–741.

Watson, A K and Wall, R E 1995. Mycoherbicides: their role in vegetation management in Canadian forests. In: Recent Progress in Forest Biotechnology in Canada (P. J. Charest and L. C. Duchesne, eds.). Canadian Forest Service Information Report PI-X-120: 74–82.

Voglelgsang, S., S. F. Shamoun and R. E. Countess. 2001. Inoculum production and biology of the fungal pathogen *Valdensinia heterodoxa*, a potential biological control agent for salal. Canadian Journal of Plant Pathology 2001, Volume 23 (2): 208–209 (Abstract), June, 2001.

We claim:

1. A biologically pure isolate of the naturally occurring fungus, *Valdensinia heterodoxa*, having all of the identifying characteristics of IDAC Deposit Accession no. IDA 180402.

2. A herbicidal composition containing as active ingredient, the biologically pure isolate according to claim 1.

3. A herbicidal composition according to claim 2, for controlling salal (*Gaultheria shallon* Pursh), wherein the active ingredient is provided as an inoculum in an agriculturally and environmentally acceptable solid growth substrate capable of supporting growth of the fungus, containing a cereal grain.

4. A composition according to claim 3, wherein the inoculum includes salal plant tissue, colonized by *V. heterodoxa*.

5. A composition according to claim 4, wherein the cereal grain is oats.

6. A method for controlling salal (*Gaultheria shallon* Pursh.), comprising applying to a salal plant or to a salal plant locus, an effective amount of a herbicidal composition containing as active ingredient, a biologically pure isolate of the fungus *Valdensinia heterodoxa* having all of the identifying characteristics of IDAC Deposit Accession no. IDA 180402.

7. A method according to claim 6, wherein the active ingredient is provided as an inoculum in an agriculturally and environmentally acceptable solid growth substrate capable of supporting growth of the fungus, containing a cereal grain.

8. A method according to claim 7, wherein the inoculum includes salal plant tissue, colonized by *V. heterodoxa*.

9. A method according to claim 8, wherein the inoculum is applied to a salal plant, below leaves.

10. A method according to claim 9, wherein the cereal grain is oats.

11. A method according to claim 7, including growing the fungus at day/night temperatures of 20/15 to 11/6° C.

12. A method according to claim 11, comprising the additional step of incubating in agar at alternating light/dark cycles.

13. A method according to claim 11, wherein the day/night temperatures are 17/12° C.

* * * * *